US008202307B2

United States Patent
Rodrigues et al.

(10) Patent No.: US 8,202,307 B2
(45) Date of Patent: Jun. 19, 2012

(54) PHOTOTHERAPY EQUIPMENT FOR THE TREATMENT OF HYPERBILIRUBINEMIA AND OTHER DISEASES

(76) Inventors: Djalma Luiz Rodrigues, São Paulo (BR); Orlando Rossi Filho, Poá (BR)

( * ) Notice: Subject to any disclaimer, the term of this patent is extended or adjusted under 35 U.S.C. 154(b) by 1534 days.

(21) Appl. No.: 11/384,224

(22) Filed: Mar. 17, 2006

(65) Prior Publication Data
US 2007/0027510 A1    Feb. 1, 2007

Related U.S. Application Data

(63) Continuation of application No. PCT/BR2004/000175, filed on Sep. 17, 2004.

(30) Foreign Application Priority Data

Sep. 17, 2003  (BR) .................................. 8302354 U
Apr. 27, 2004  (BR) .................................. 8400812 U

(51) Int. Cl.
A61N 5/06    (2006.01)
(52) U.S. Cl. .................... 607/88; 607/91; 606/2; 606/19
(58) Field of Classification Search .............. 607/88, 607/91; 606/2–19
See application file for complete search history.

(56) References Cited

U.S. PATENT DOCUMENTS

| 5,551,949 | A  | * | 9/1996  | Kim ................................ 601/15 |
| 5,698,866 | A  |   | 12/1997 | Doiron et al. |
| 6,221,095 | B1 | * | 4/2001  | Van Zuylen et al. ............ 607/88 |
| 6,270,244 | B1 | * | 8/2001  | Naum ............................ 362/583 |
| 6,290,713 | B1 | * | 9/2001  | Russell ............................ 607/88 |
| 6,331,111 | B1 | * | 12/2001 | Cao ................................. 433/29 |
| 6,359,292 | B1 | * | 3/2002  | Sugawara et al. ............. 257/103 |
| 6,596,016 | B1 |   | 7/2003  | Vreman et al. |
| 2001/0053907 | A1 | * | 12/2001 | Ota ................................. 606/10 |
| 2002/0121646 | A1 | * | 9/2002  | Khare et al. ................... 257/103 |

FOREIGN PATENT DOCUMENTS

| EP | 0 320 080     | 6/1989 |
| EP | 1 138 349 A2  | 10/2001 |
| WO | WO 2004/032714 | 4/2004 |
| WO | WO 2004/033028 | 4/2004 |
| WO | WO 2004/033029 | 4/2004 |

OTHER PUBLICATIONS

Vreman et al., "Light-Emitting Diodes: A Novel Light Source for Phototherapy," Pediatric Research, vol. 44, No. 5, Nov. 1998, pp. 804-809, XP008039999.

(Continued)

Primary Examiner — Aaron Roane
(74) Attorney, Agent, or Firm — Alston & Bird LLP

(57) ABSTRACT

The present invention relates to a phototherapy equipment, provided with at least one super LED of high luminous radiation, whose application is the treatment of hyperbilirubinemia, constituted by a luminous source formed by a split compact and elongated housing, provided, in its lower and front portion, with a cover containing internally adjustable lenses having one or more phototherapic sources with very high luminous irradiation at blue spectral range, more accurately in the wavelength of 450 nm, containing in the upper part a fan and electrically connected with a microprocessed circuit, which is able to be adjusted through control and programming actuators, having its functions monitored by means a display and a connector for any sensor, or digitized through a connection with a microcomputer.

18 Claims, 14 Drawing Sheets

OTHER PUBLICATIONS http://ledmuseum.home.att.net/agilent.htm, "Luxeon Star/Barracuda/Prometheus, Luxeon Star Power Light Source," retrieved from internet on May 16, 2006, relevant pp. 3/21, 4/21 and 8/21.
International Search Report and Written Opinion of corresponding international Application No. PCT/BR2004/000175, mailed Dec. 27, 2004.

Written Opinion of corresponding international Application No. PCT/BR2004/000175, mailed Sep. 30, 2005.
International Preliminary Report on Patentability of corresponding international Application No. PCT/BR2004/000175, completed Dec. 19, 2005.

* cited by examiner

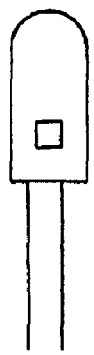
Fig. 11
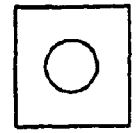
Fig. 12
Fig. 13
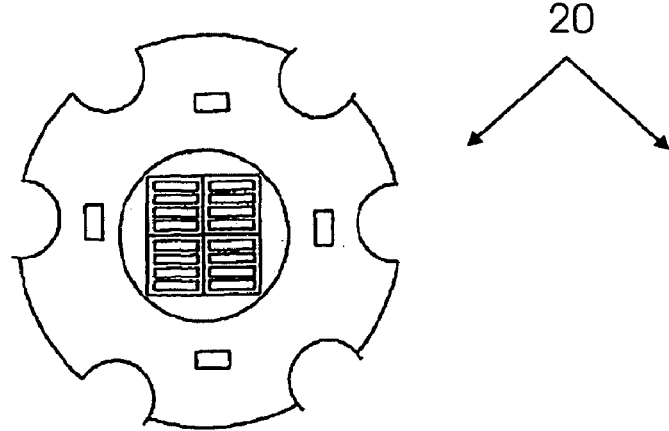
Fig. 14
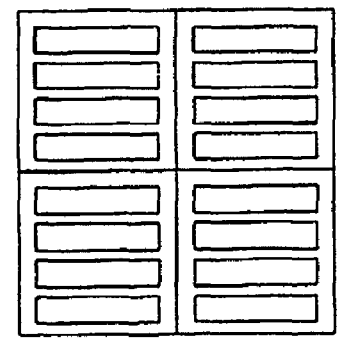

PHOTOTHERAPY EQUIPMENT FOR THE TREATMENT OF HYPERBILIRUBINEMIA AND OTHER DISEASES

CROSS-REFERENCE TO RELATED APPLICATIONS

This application is a continuation of International Patent Application PCT/BR2004/000175 filed Sep. 17, 2004, which designated the United States and was published under PCT Article 21(2) in English, and which is hereby incorporated herein in its entirety by reference.

BACKGROUND OF THE INVENTION

1) Field of the Invention

The instant invention refers to phototherapy equipment, particularly for the treatment of hyperbilirubinemia, designed to deliver excellent performance and high operational flexibility and safety due to its unique construction, consisting of a small number of blue-spectral-high-radiation light emission diodes (LED's), with advanced microprocessing and communication capacity with other equipment, everything in reduced sized and easily handled.

2) Description of Related Art

Phototherapy is normally used in the treatment of neonatal hyperbilirubinemia, being the patient exposed to radiation focused on the visible light blue spectrum for a time to be determined according to the healthcare professional in charge.

Hyperbilirubinemia is a syndrome that affects a lot of newborns, corresponding to the incapacity of the infant of metabolizing and eliminating the bilirubin pigment from its blood stream accordingly. At high doses in the blood, bilirubinemia makes the infant to present yellowish color of the skin and, in the most critical events, it can generate neuromuscular and cognitive development impairment in the infant.

The newborns phototherapy treatment significantly reduces the levels of bilirubin. Basically, the light emitted by the phototherapy equipment enables to transform bilirubin into other substances more easily eliminated by the body through photo-oxidation, configurational isomerization, and structural isomerization.

The introduction of phototherapy in the treatment of neonatal bilirubinemia since its advent in the late 1950's and later by virtue of the great evolution in the types of the lamps used, has minimized the risks, without, however, eliminating the adverse side effects of the ultraviolet rays and infrared rays on the patient's body. This occurs because the conventional light sources (lamps) not only generate it in the efficient spectrum for the treatment, but also emits infrared and ultraviolet rays that are harmful to the patient's body.

With the advance of the electronic technology in the illumination field, we now have components that help engineering in developing better, more efficient and safer medical equipment, mainly when it comes to saving human lives. The use of different types of lamp in the treatment of newborns is world-widely used, and the benefits of this treatment are unquestionable.

The first phototherapy apparatus used fluorescent lamps, which produced a more efficient phototherapeutic effect than the irradiation of light by means of ordinary lamps, since they emit a high rate of "cold" luminous radiation, that is to say, a whiter light spectrum. However, the level of irradiation of fluorescent lamps was very low, and it was necessary to use a large number of lamps simultaneously, which would require the use of a large-size apparatus so that the radiating energy could be sufficient for the desired healing effect.

In order to overcome this serious drawback, one researched and studied the application of high-irradiance fluorescent blue lamps, developed and manufactured with the main purpose of being used on phototherapy apparatus. However, although these lamps emitted light with properties more suitable for the implementation of phototherapy, when compared to the ordinary incandescent lamps, they still had the outstanding disadvantage of exhibiting long wave length, occupying enormous spaces in the newborn Intensive therapy units in the hospitals.

With the advance of technology, halogen lamps were introduced into the market, which are lamps having filament enclosed in a halogen gas atmosphere that have a performance very superior to that of fluorescent lamps (notwithstanding the higher power consumption) in the treatment of hyperbilirubinemia, with a quite reduced size. This type of lamp, however, produces much heat and has a relatively short useful life (about 2,000 hours), and should be replaced at intervals shorter than desirable.

As a consequence, phototherapy equipment that operates with halogen lamps should have some kind of refrigeration system, by means of fans, and infrared and ultraviolet rays filters, in order to reduce the undesirable effects to the newborn's body.

In order to eliminate the excess heat caused by the phototherapeutic luminous irradiation with halogen lamps, the technology evolved to the application of solid state lamps or ordinary blue LED's (light emission diodes). The LED's are capable of generating a lot of luminosity despite their size and they do not heat much, which is a surprise when compared to the luminosity they generate.

However, due to their reduced size, the conventional LED's do not have good irradiation if considered unitarily. In order to obtain a satisfactory treatment effect, many LED's should be used in conjunction and the equipment should be placed very close to the patient's body.

LED's phototherapy equipment is, therefore, limited to some applications where it is necessary to position the source of light very near to the patient.

A landmark in the use of LED's for the treatment of hyperbilirubinemia is the article of the American journal "*Pediatric Research*" of November, 1998 (volume 44, number 5), which provides on the use of LED's in the treatment of hyperbilirubinemia and suggests the use of two light sources of different wave lengths used simultaneously during the procedure. The method disclosed in this article predicts the combination of one hundred (100) LED's series combination (preferably three series) where the light overlay of the different wave lengths would enable a large amount of light radiation, which does not happen with the other kinds of conventional light sources tested. The great inconvenient of this treatment, however, is that in order to obtain the appropriate radiation for the hyperbilirubinemia treatment, it is necessary a very large amount of LED's (three hundred total). Therefore, the resulting equipment is considerably large and expensive, both in terms of manufacturing and operation (due to the need of installation and feed of the 300 LED's with electric power).

This first document of the prior art does not report details of the phototherapy equipment used, but only the first experience using LED's in the treatment of hyperbilirubinemia. Anyhow, it is worth noting that this scientific paper proved the viability and efficacy of the use of LED's, which led several manufacturers to develop phototherapy equipment with more developed and efficient LED's.

Notwithstanding, in 1997, U.S. Pat. No. 5,698,866, was granted to a phototherapy equipment having LED's for the production of luminosity, although the object of this patent is the use of lens and collimators to properly direct the light produced by the LED's. FIGS. 1 and 4 show that the operational area of the several LED's is limited, since they are positioned on the edge of a small hand piece. The equipment thereof was not idealized for the treatment of hyperbilirubinemia.

A second study on phototherapy with LED's, now published in the American journal specialized in the medical area, "*The Journal of Pediatrics*" (June/2000, volume 136 and number 6), shows an experience with 69 patients for the treatment of hyperbilirubinemia through a prototype phototherapy equipment (the photography of which can be seen in the article). The prototype equipment contains 6 sets with one hundred (100) blue LED's of gallium nitride each, which radiate the light as far as approximately 20 cm from the patient. Since this equipment comprehends a large amount of blue LED's (six hundred), it is intrinsically expensive, large (which limits its handling over the patient) and difficult to operate (high electric power consumption).

Another phototherapy equipment for the treatment of hyperbilirubinemia is disclosed on documents WO 2004/033028 and WO 2004/033029 and comprehends a plurality of LED's that emit light in the blue spectrum (efficient when transforming bilirubin) and, in addition, a few LED's that emit light in the yellow spectrum, with a view to eliminate the feelings of nausea caused by the LED's that emit blue light. As mentioned in the document, the equipment uses something like one thousand (1,000) LED's that emit light in the blue-green visible spectrum for the treatment of hyperbilirubinemia together with approximately three hundred and twenty (320) LED's emitting yellow light to minimize the discomforts caused by the blue light, that is, approximately one thousand, three hundred and twenty (1,320) LED's to radiate an appropriate amount of light for the treatment.

The drawbacks arising from the large number of LED's presented in the equipment are the high manufacturing and operational costs (high power consumption, high replacement cost of the over 1,300 LED's in the end of their useful life), and the significant dimensions, due to the large number of existent LED's, limiting the equipment positioning mobility regarding the newborn under treatment.

Another example of equipment used for the treatment of hyperbilirubinemia that has a plurality of conventional LED's is present in document WO 2004/032714. This equipment has a light diffusing panel that enhances the uniformity of exposure of the patient to light, by using a plurality of LED's arranged in series and in an non-uniform manner, and also has a directing mechanism that guarantees its positioning always in a correctly aligned manner over the patient, so that the incident light can be adequate.

However, like the equipment mentioned before, this one uses about seven hundred fifty (750) LED's that emit light in the visible blue-green spectrum for the treatment of hyperbilirubinemia, making it very expensive and with very large dimensions due to the great number of LED's that should be accommodated on the light diffusing panel. Evidently, the drawbacks of high manufacture and operational cost of this equipment also are significant.

Still, another phototherapy equipment for the treatment of hyperbilirubinemia is showed on document EP 1 138 349, and includes a plurality of LED's for the generation of luminosity, being that these LED's can be positioned in flexible structures that enable its placement around the patient's body.

Finally, another relevant prior art, of the same author of the article of the American journal "*Pediatric Research*" of November, 1998, is the North-American U.S. Pat. No. 6,596,016, which shows phototherapy equipment for the treatment of hyperbilirubinemia comprehending a flexible base to which are associated a plurality of LED's, which creates all inconvenient already mentioned for the other previously analyzed equipment.

Every equipment for the treatment of hyperbilirubinemia provided with the LED's currently available present some or all drawbacks of being large, heavy and very expensive, whether regarding the manufacture or the operation, which makes its handling close to the patient difficult, thus causing extremely high expenses for the hospitals and clinics that use them.

BRIEF SUMMARY OF THE INVENTION

A first objective of the present invention is to provide a phototherapy equipment for the treatment of hyperbilirubinemia, provided not with LED's that emit light in the blue spectrum known at present, but with a different type of LED (composed by Nitride of Gallium and Indium—InGaN), which exhibits extremely high luminous irradiation in the specific range of the blue color, more precisely in the wave length of 450 nm, without using filters. Thus, the equipment can exhibit an extremely reduced number of super LED's in comparison with the number of conventional LED's required.

Another objective of the present invention is to provide phototherapy equipment especially designed and developed to obtain great handiness, since it has a processor element (microprocessor) and that has great advantages, in both use and manufacture.

A further objective of the present invention is to provide a model of phototherapy equipment that is inexpensive to be industrially implemented, meeting the requirements of robustness, safety and handiness, thus providing the healthcare professionals and even the patients with an additional option on the market of this kind of equipment, which, unlike the present-day models, offers numberless possibilities and benefits to the users, thus becoming a model of great acceptance on the consumer market.

The objectives of the present invention are achieved by means of a phototherapy equipment, designed for the treatment of hyperbilirubinemia and other diseases, comprising at least one body provided with at least one phototherapic light source, in the form of at least one LED composed of Nitride of Gallium and Indium (InGaN), and at least one internal processing element, such as a microprocessor (microchip), wherein the LED comprises three individual LEDS inscribed or wrapped by a collimator.

The objectives of the present invention are also achieved by means of a phototherapy equipment, designed for the treatment of hyperbilirubinemia and other diseases, comprising at least one body provided with at least one phototherapic light source, in the form of at least one LED composed of Nitride of Gallium and Indium (InGaN), and at least one internal processing element, such as a microprocessor (microchip), wherein the LED comprises three individual LED's without energy-dissipating aluminum either inscribed or wrapped by a collimator.

The objectives of the present invention are also achieved by means of a phototherapy equipment, designed for the treatment of hyperbilirubinemia and other diseases, comprising at least one body provided with at least one phototherapic light source, in the form of at least one LED composed of Nitride of Gallium and Indium (InGaN), and at least one internal processing element, such as a microprocessor (microchip), wherein it further comprises a management system for the equipment, whose operation is enabled by the microprocessor.

The objectives of the present invention are also achieved by means of a phototherapy equipment, designed for the treatment of hyperbilirubinemia and other diseases, comprising at least one body provided with at least one phototherapic light source, in the form of at least one LED composed of Nitride of Gallium and Indium (InGaN), and at least one internal processing element, such as a microprocessor (microchip), wherein it further comprises a computer program, enabling to provide the information regarding lifetime of LED before the light properties it emits may suffer deterioration.

The objectives of the present invention are also achieved by means of a phototherapy equipment, designed for the treatment of hyperbilirubinemia and other diseases, comprising at least one body provided with at least one phototherapic light source, in the form of at least one LED composed of Nitride of Gallium and Indium (InGaN), and at least one internal processing element, such as a microprocessor (microchip), and at least one connector for association of at least one sensor, wherein it further comprises a computer program, enabling to process information provided by the sensor and the display of processing result.

The objectives of the present invention are also achieved by means of a phototherapy equipment, designed for the treatment of hyperbilirubinemia and other diseases, comprising at least one body provided with at least one phototherapic light source, in the form of at least one LED composed of Nitride of Gallium and Indium (InGaN), and at least one internal processing element, such as a microprocessor (microchip), wherein it further comprises at least one memory element.

The objectives of the present invention are also achieved by means of a phototherapy equipment, designed for the treatment of hyperbilirubinemia and other diseases, comprising at least one body provided with at least one phototherapic light source, in the form of at least one LED composed of Nitride of Gallium and Indium (InGaN), and at least one internal processing element, such as a microprocessor (microchip), and at least one connector for communication with a microcomputer, wherein the connector is an electromagnetic wave transmitting antenna.

The objectives of the present invention are also achieved by means of a phototherapy equipment, designed for the treatment of hyperbilirubinemia and other diseases, comprising at least one body provided with at least one phototherapic light source, in the form of at least one LED composed of Nitride of Gallium and Indium (InGaN), and at least one internal processing element, such as a microprocessor (microchip), and at least one connector for association with at least one sensor, wherein it further comprises a computer program which enables irradiance adjustment.

The present invention has the following vantages:

(i) considerable decrease in the number of components and the size of the equipment, enabling low costs of manufacture, maintenance, operation and ease to handle, use and positioning on cradles, incubators, etc.;

(ii) low consumption of electricity, by virtue of the existence of few LED's, which makes the use of batteries feasible (iii) long useful life of the LED's, in comparison with the conventional halogen or fluorescent lamps;

(iv) emission of light in the blue spectrum, precisely in the wave length of 450 nm, with high values of radiance, which makes unnecessary the existence of filters for controlling infrared and ultraviolet rays;

(v) considerable reduction of the heat emitted, enabling the elimination of lenses for enhancing its efficiency;

(vi) possibility of using the equipment in households, since it does not emit infrared and ultraviolet rays;

(vii) focus of the light on the patient's body in a more defined and homogeneous manner, in the form of an ellipsis of larger area, with lesser loss at the borders, thus enabling a more anatomical application to the patient's body; and (viii) beautiful and attractive design, decreasing the oppression of the treatment.

BRIEF DESCRIPTION OF THE DRAWINGS

The present will now be described in greater detail with reference to an embodiment represented in the drawings. The figures show:

FIG. 11—is a first schematic view of a conventional Gallium Nitride (GaN) LED, provided with a single chip of semi-conductor element.

FIG. 12—is a second schematic view of a conventional LED, showed in FIG. 11.

FIG. 13—is a first schematic view of a LED variation, that can be used in the equipment hereof, composed by Nitride of Gallium and Indium (InGaN), provided with 4 blocks with 4 individual LED's on a chip.

FIG. 14—is a second schematic view of the Nitride of Gallium and Indium LED showed in FIG. 13.

DETAILED DESCRIPTION OF THE INVENTION

Figure 1:
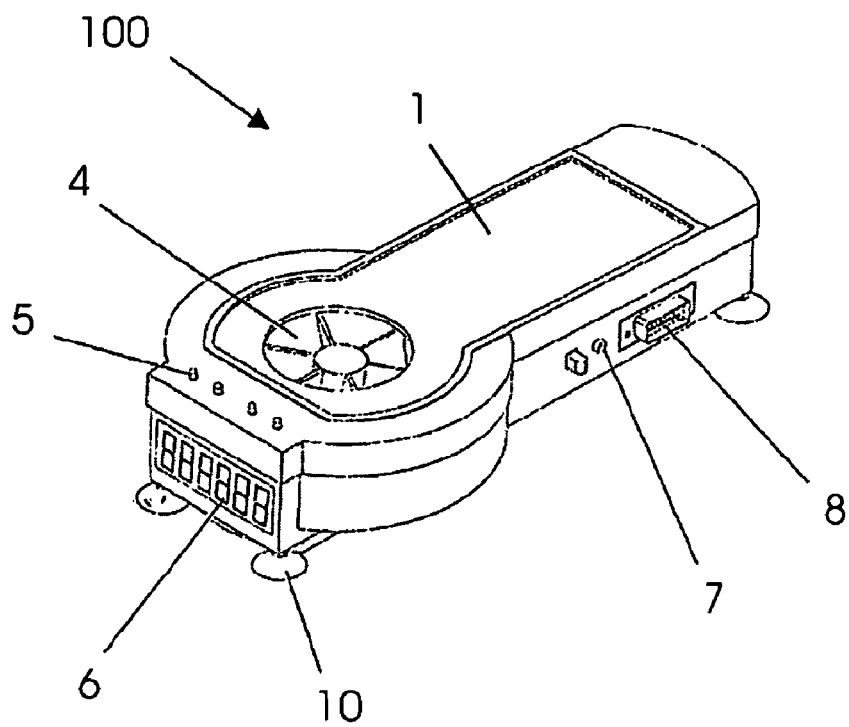
FIG. 1—is a top perspective view of the phototherapy equipment of the present invention.
Figure 2:
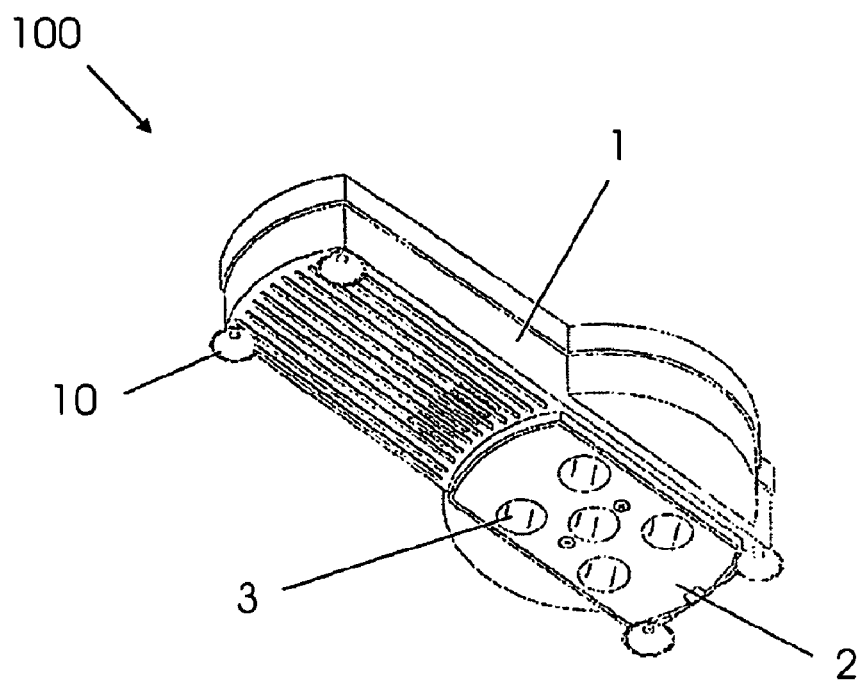
FIG. 2—is a bottom perspective view of the phototherapy equipment showed on FIG. 1.

According to a preferred embodiment and as can be seen in FIGS. 1 to 10, the phototherapy equipment 100 of the present invention is essentially constituted by a base of luminous source, formed by a split, compact, elongate housing 1, provided with at least one phototherapeutic source of light of very high luminous irradiation in the spectral range of blue color, more precisely in the wave length of 450 nm, and which will be mentioned more thoroughly later on. It is optionally provided with a cooler (fan) 4 and at least one internal battery (not showed).

In order to provide its operation, the phototherapeutic equipment 100 still count on a microprocessed circuit (which will also be described more thoroughly later) that can also be adjusted by control and programming or remote programming triggers 5, being its functions monitored by a visor 6, and a connector 7 for an optic sensor, or digitalized by means of a connection 8, attached to a microcomputer or other similar equipment.

The phototherapeutic equipment 100 now showed can have applications in medical instrumentation, in order to treat hyperbilirubinemia and other diseases that can be treated with phototherapy.

Regarding the aspect of equipment 100, the housing 1 (which corresponds to the body of the equipment), may have any necessary or desirable shape, as well as be made from the most varied materials, such as diverse polymers, metals, etc.

Preferably, the body 1 is substantially parallelepiped-shaped, comprising a first substantially cylindrical free end (wherein the diameter of the circumference is substantially larger than the width of the body 1, creating two semicircular side projections) and at least one aperture in its main face to enable passage of air to be sucked and moved by the cooler 4. Alternatively, one may foresee a static dissipater with tabs, without a cooler to force circulation of air, or even, any other solution that enables the heat transfer between the LED's 20 and the environment.

At the first substantially cylindrical free end, it is preferably provided at least one control panel 6, preferably in the form of a display, which enables the correct monitoring and handling of the equipment 100. This display 6 is preferably an alphanumeric liquid-crystal display (LCD), which enables one to read messages, but may assume any other configurations, such as a panel with warning lamps, a small keyboard or any another functional solutions. Evidently, if required or desirable, it is possible to optimize the equipment 100 according to the provisions hereof without any kind of display.

In at least one of its lateral portions, the body 1 comprises at least one connector 7 for an optical sensor (which will be described later) and at least one connector for communication with a microprocessor 8, such as a connector RS-232, an USB connector or any other functional one. The equipment may even have a connector in the shape of an electromagnetic wave transmission antenna. Evidently, the body 1 may have these connectors positioned in a portion other than the lateral ones, and one may further provide other elements that enable the equipment 100 to function and operate, such as an ON-OFF button, luminosity intensity control, handles, etc.

The equipment 100 hereof can be expected to connect with information networks, such as intranet or even connected to the Internet, when a large information traffic will be able to happen between the equipment 100 and remote computers. It is worth noting that the equipment 100 connection with these information networks can be made physically (cabling) as well as wirelessly (wi fi). Therefore, it is possible, for instance, to control several phototherapy equipments 100 from a central room of a maternity, being the nurse waived from following the patient on a full-time basis. The operation of equipment 100, which enables this kind of thing, will be described later.

Finally, in its second main face, opposite to the first one, bores are provided for the passage of the luminosity produced by the LED's 20. By preference, body 1 comprises five apertures positioned in H-arrangement, but it is evident that these characteristics may vary. Further by preference, the apertures enclose lenses 3, which are internally adjustable and conveniently enable one to handle the properties of the emitted light for the purpose of directing them correctly and change the application area of the phototherapy. Additionally or alternatively to the 3 internally adjustable lens, the equipment 100 can comprehend any other mean to better direct the light generated by the LED's 20 over the body of the newborn under treatment, such as an adjustable optic device, as well as it can use different filters, lens, or any other element required or desirable to favorably manipulate the radiated light (for instance, a collimator—mirrored lens or directing device—of light in a limited area for better improvement of the light together with each LED, besides a frontal reflection mirror or like a overhead projector (mirror behind the LED).

It should be noted that, in order to enable one to handle the equipment (for instance, replacement of LED's 20), the body 1 comprises a cover 2, preferably positioned in the second main face.

The LED's 20 used on the equipment 100 of the present invention are different from the conventional LED's made of gallium nitride (GaN) showed in FIGS. 11 and 12, as well as regarding the LED's of the phototherapy equipment disclosed on all prior art documents, since they are composed of Indium and Gallium Nitride (InGaN), and emit a high power light in a small visible range of the (blue) electromagnetic radiation spectrum, without infrared radiation. The led 20 of Indium and Gallium Nitride (InGaN), whatever is its particular constitution, is commercially named "Super LED".

For information purposes, the conventional LED's, due to their low density energy, do not need a body to dissipate the potency, what makes them very compact. Their construction is made with a chip and one single LED covered by a clear acrylic body; their terminals leave by the bottom of the acrylic body.

A first type of LED composed by Indium and Gallium Nitride, used in the equipment 100 is schematically showed in FIGS. 13 and 14 and consists of 16 LED's in a same chip (high-scale integration), forming four blocks of 4 LED's each. The chip of this LED is deposited through a dense film onto a star-shaped aluminum plate, in order to provide better dissipation of power. The body of the super LED has terminals arranged on the surface of the film over the aluminum. This first kind of LED used is manufactured by the company Luxeon®.

The equipment 100, when equipped with the five LED's described above have the following characteristics:

Light emission in the blue spectrum focused on 460 nm, being no light ray emission observed in the infrared and ultraviolet light. Therefore, it is not necessary to use filters for these wave lengths, which makes the equipment cheaper (see graphic 1 below).

Light intensity (considering the average in the luminous focus center 30 centimeters way) between 35 and 40 µW/cm² nm (see graphic 2 below).

Dimension of the luminous focus between 30 centimeters and 40 centimeters.

Body temperature increase of the patient inferior to 1.5° C., considering a room temperature of 25° C.

Very low noise, inferior to 50 dB.

Comparatively, conventional phototherapy equipment equipped with amount superior to 200 common LED's of Gallium Nitride (GaN) enables light intensity of 35 µW/cm² nm.

Still on a comparative basis, to explain the advance of the equipment 100 hereof, phototherapy equipment that use halogen and fluorescent lamps enable light intensity, respectively at the range of 25 µW/cm² nm and 4 µW/cm² nm (se graphic 3).

Finally, graphic 2 enables the visualization of the ratio showed between the application distance and the light focus of the equipment 100. It can be observed that the light intensity is considerable event far away from the application, as far as 50 centimeters, and that the application area is elevated even at short distances, such as 20 centimeters.

This first kind of LED is already used in odontological equipment for polymerization of resins, however, it had never been used in phototherapy for the treatment of hyperbilirubinemia and other diseases.

A second kind of LED 20 that can be used, also Indium and Gallium Nitride (InGaN), actually corresponds to three individual LED's inscribed in or involved by a same collimator. Due to the technical-conceptual enhancements, this improved LED does not need an aluminum plate to dissipate power therefore, being much more compact than the LED 20 showed in FIGS. 13 and 14.

The three individual LED's ignite and provide a high intensity light, in the desired blue spectral frequency, making the resulting ensemble highly attractive for using the equipment 100 that presents compact dimensions.

Figure 15:
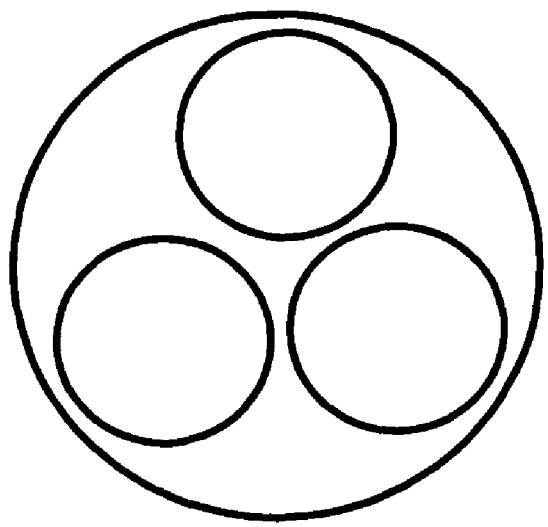
FIG. 15—is a first schematic view of a LED variation that can be used in the equipment hereof, composed by three individual LED's of Nitride of Gallium and Indium (InGaN) inscribed in the same collimator.
Figure 16:
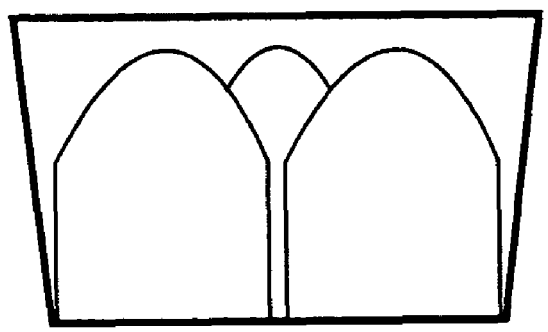
FIG. 16—is a second schematic view of the LED showed in FIG. 15.

The collimator in which the three individual LED's are involved has the main function of directing all light rays emitted by each one of them towards the focus, maximizing the luminosity. Optionally, on the clear surface of this improved LED, to where all light rays produced are directed, at least one lens is provided in order to change the properties of the luminosity focus. For instance, a lens can be used to increase or reduce the area of the light focus, direct or reduce the percentage of light into the central portion of the focus, etc. A schematic view of this improved LED is available in FIGS. 15 and 16.

Evidently, several variations on this improved LED can be conceived, such as, varying the individual LED's amount (one, two, four, five, etc.), the positioning of these LED's inside the collimator (which will change the light distribution), the shape of the collimator, among other innumerous possibilities. With these changes, one can obtain LED's with very different properties regarding the intensity of the light emitted, which increases the possibilities for an optimized model to be used in the equipment 100 be found.

Preferably, the second LED 20 also emits light with wave lengths of 450 nm, making unnecessary the installation of filters for controlling the light emitted, since there is no emission of ultraviolet or infrared rays.

No matter what is the particular configuration of the LED 20 used, as mentioned before, preferred embodiment of the equipment 100 of the present invention uses five LED's 20, which manage to generate enough light for the correct treatment of newborns who suffer from hyperbilirubinemia, but it is evident that this number may vary for more or for less, if necessary. However, even if more than five LED's 20 are used, this number will never come close to the hundreds of LED's required by the pieces of equipment known at present, due to the considerably greater power of Indium and Gallium Nitride (InGaN) LED's 20. The equipment subject matter hereof, provided with hundreds of Indium and Gallium Nitride (InGaN) LED's 20, would emit light with such intensity that it could not be safely used in phototherapy.

With the small number of Indium and Gallium Nitride (InGaN) LED's 20 necessary for the equipment 100 to be functional, it may be made small, so that it can be easily fixed to support apparatus, such as incubators 9, heated cradles or even ordinary cradles 12, placed at the mother's side, enabling the physician or the nurse to have more room for examining and working close to the patient, besides enabling the use thereof for treatment at the patient's house in order to reduce the risks. Additionally, the equipment 100 may also be arranged in a region below the patient, as for instance on the mattress itself, besides the possibility of being mounted on an independent body of the support devices, on tripods or supports.

By preference, the phototherapy equipment 100 comprises four suction pads 10, located in the second main portion of the body 1, so that it can be supported and fixed on or under incubators 9, and has means for fixing the system of articulable arm 11, which enables moments for better utilization of the light over the patient, enabling adjustment of focus on the patient.

As mentioned before, the phototherapy equipment 100 may be fixed at the end of a movable rod 13 with varying height, and having a column 14 and a pedestal 15 with turning castors, which is used for correctly adjusting the distance between the patient and the light emitters, providing excellent stability in the displacement movements.

Therefore, the equipment 100 hereof has such reduced dimensions that it has become portable equipment, unlike the apparatus known at present. As a comparison, the pieces of equipment with fluorescent lamps used to measure approximately 81 cm×40 cm; the equipment with conventional LED's measures approximately 50 cm×25 cm, and the novel equipment 100 measures only about 23 cm×12 cm.

Figure 3:
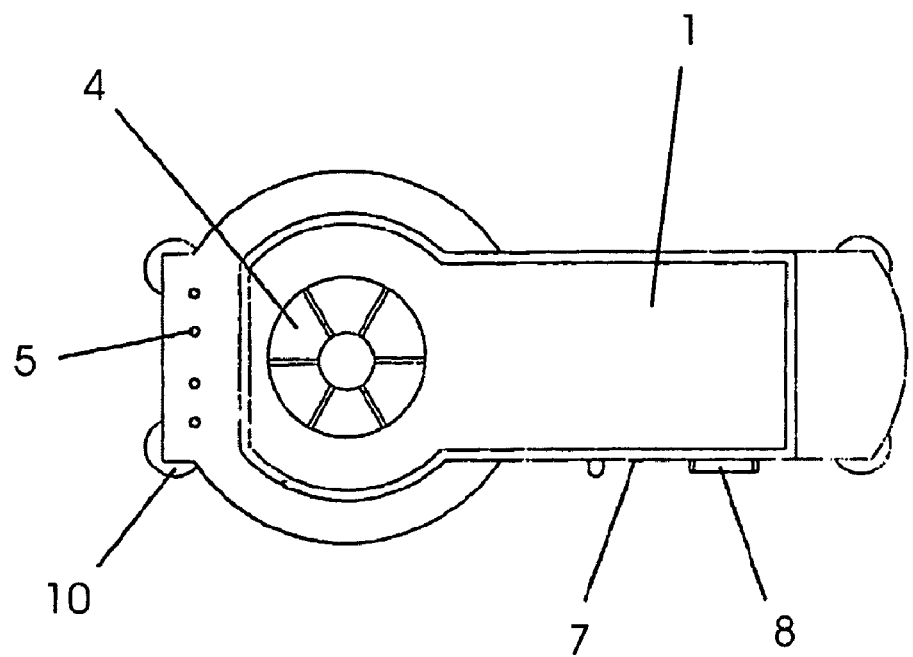
FIG. 3—is a top view of the phototherapy equipment showed on FIGS. 1 and 2.
Figure 4:
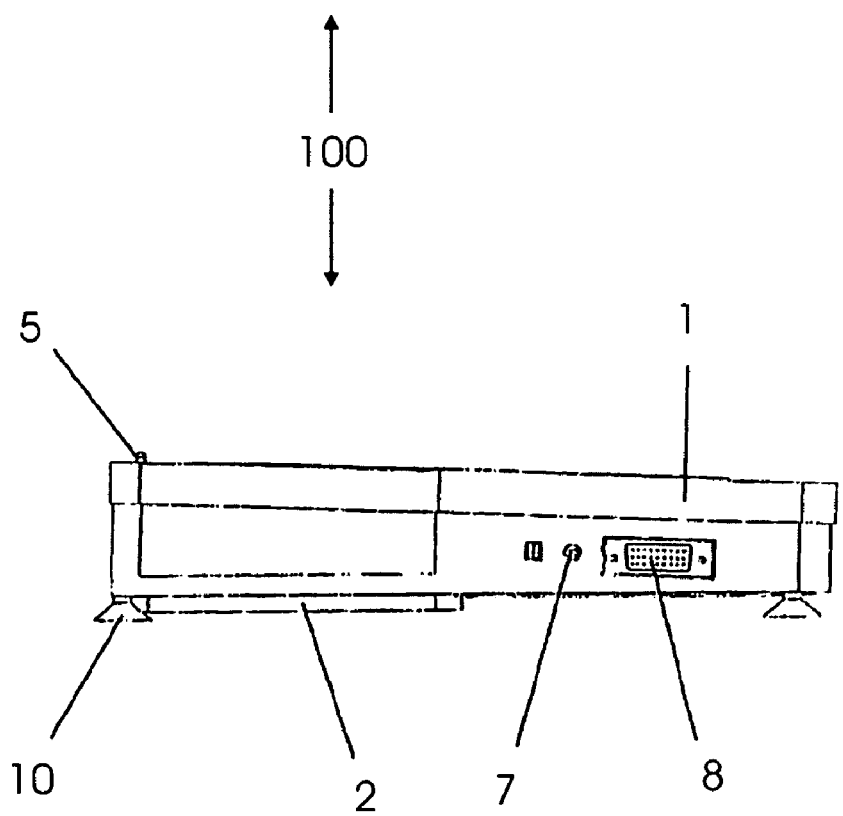
FIG. 4—is a first side view of the phototherapy equipment showed in FIGS. 1 to 3.
Figure 5:
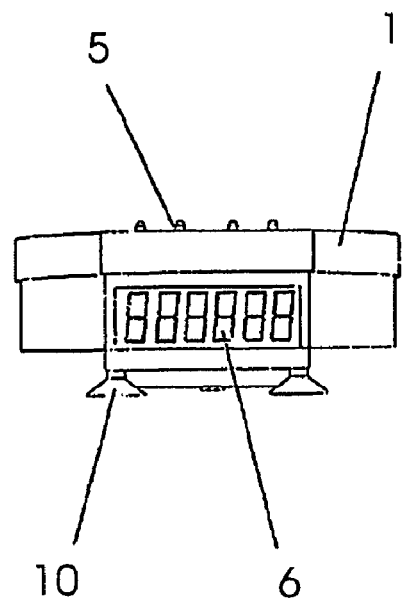
FIG. 5—is a front view of the phototherapy equipment showed on FIGS. 1 to 4.
Figure 6:
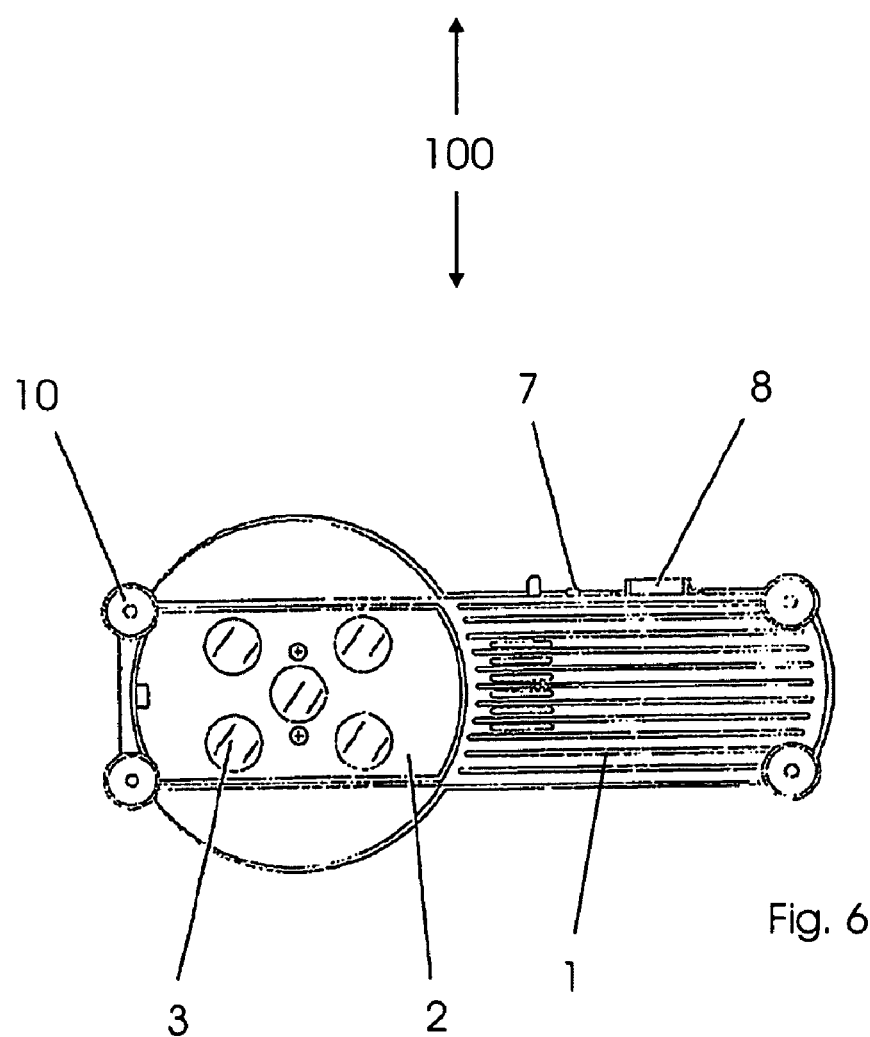
FIG. 6—is a bottom view of the phototherapy equipment showed in FIGS. 1 to 5.
Figure 7:
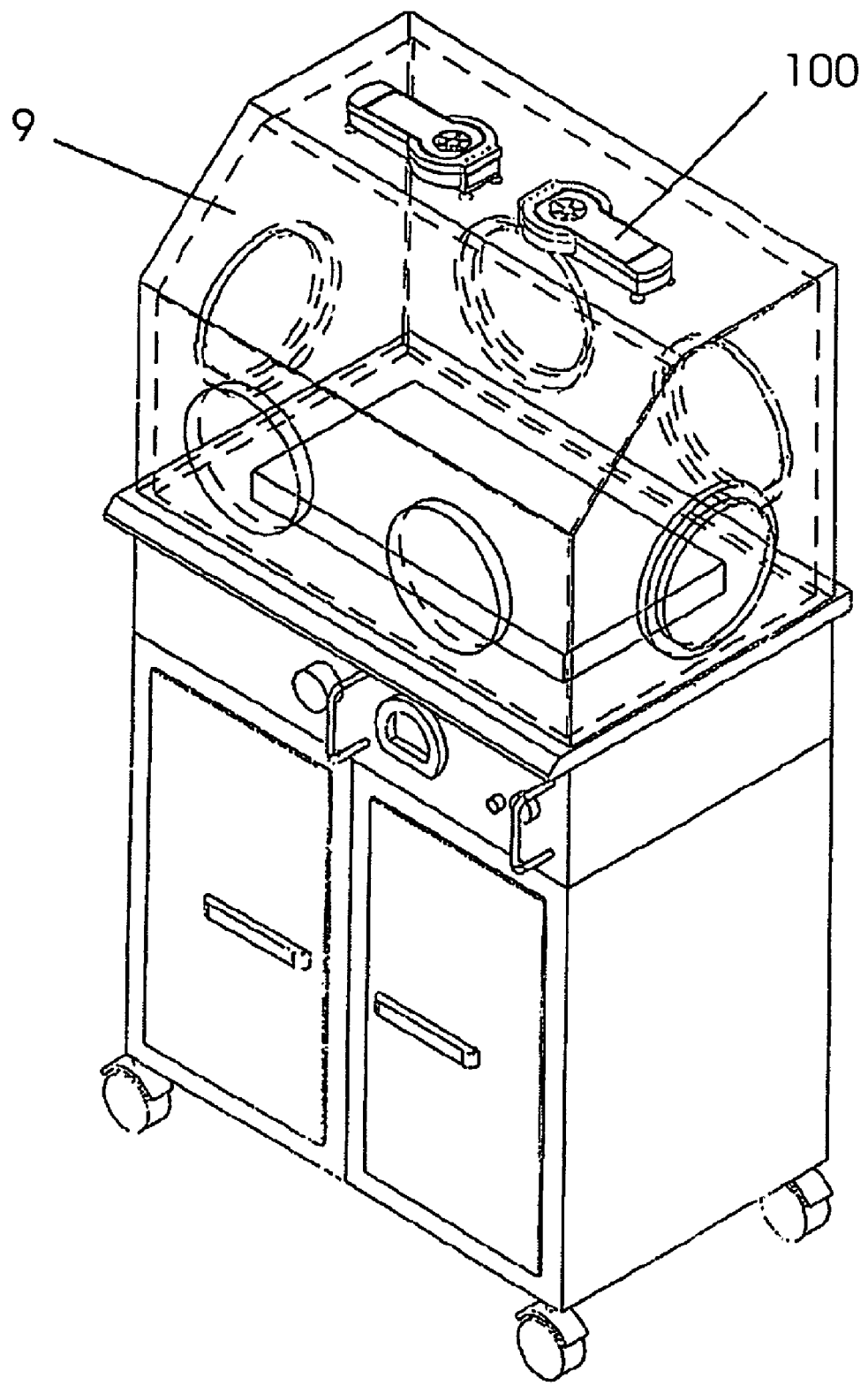
FIG. 7—is a perspective view of a generic incubator for the treatment of newborns, equipped with two phototherapeutic pieces of the equipment subject matter hereof.
Figure 8:
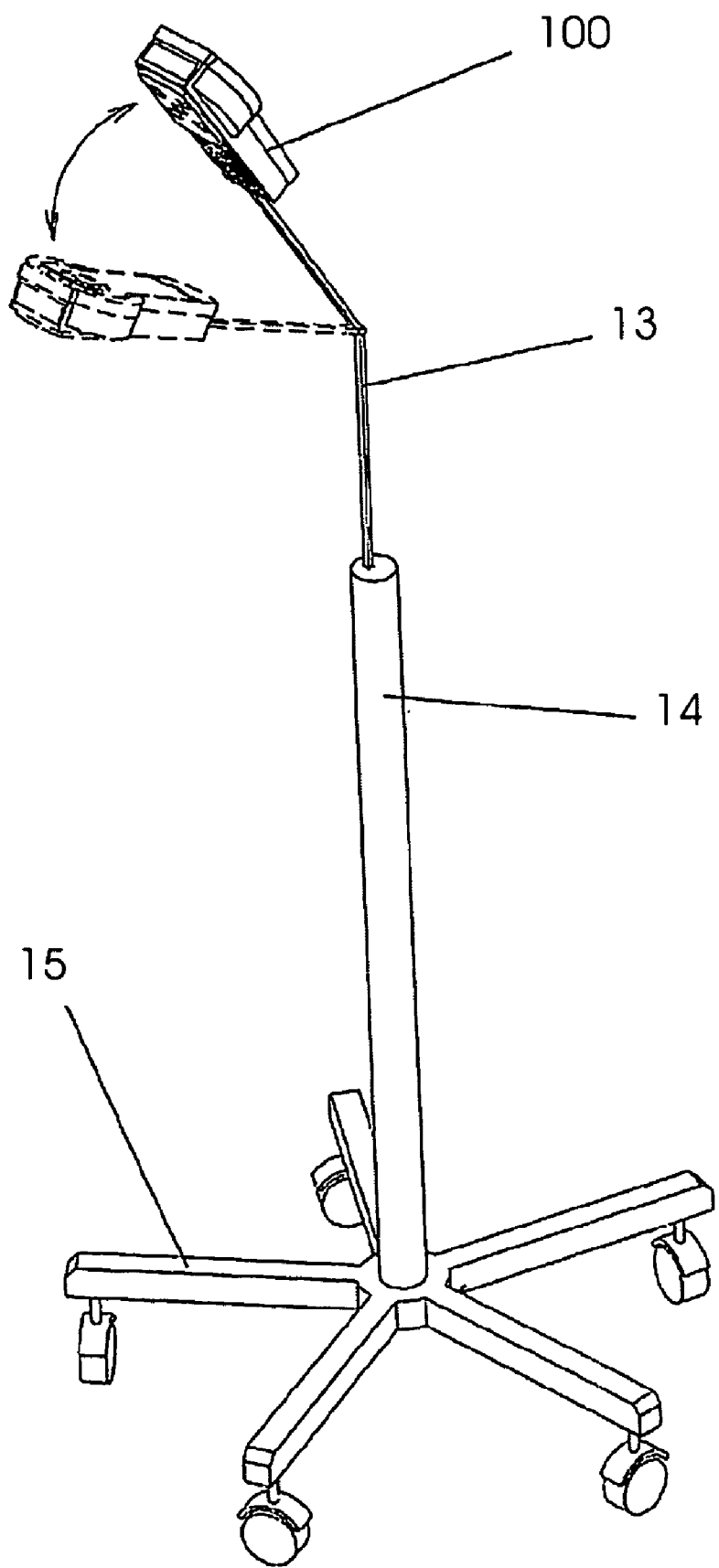
FIG. 8—is a perspective view of the phototherapeutic equipment of the present invention, positioned at the end of a movable rod, with variable height, provided with a column and a pedestal having turning castors.
Figure 9:
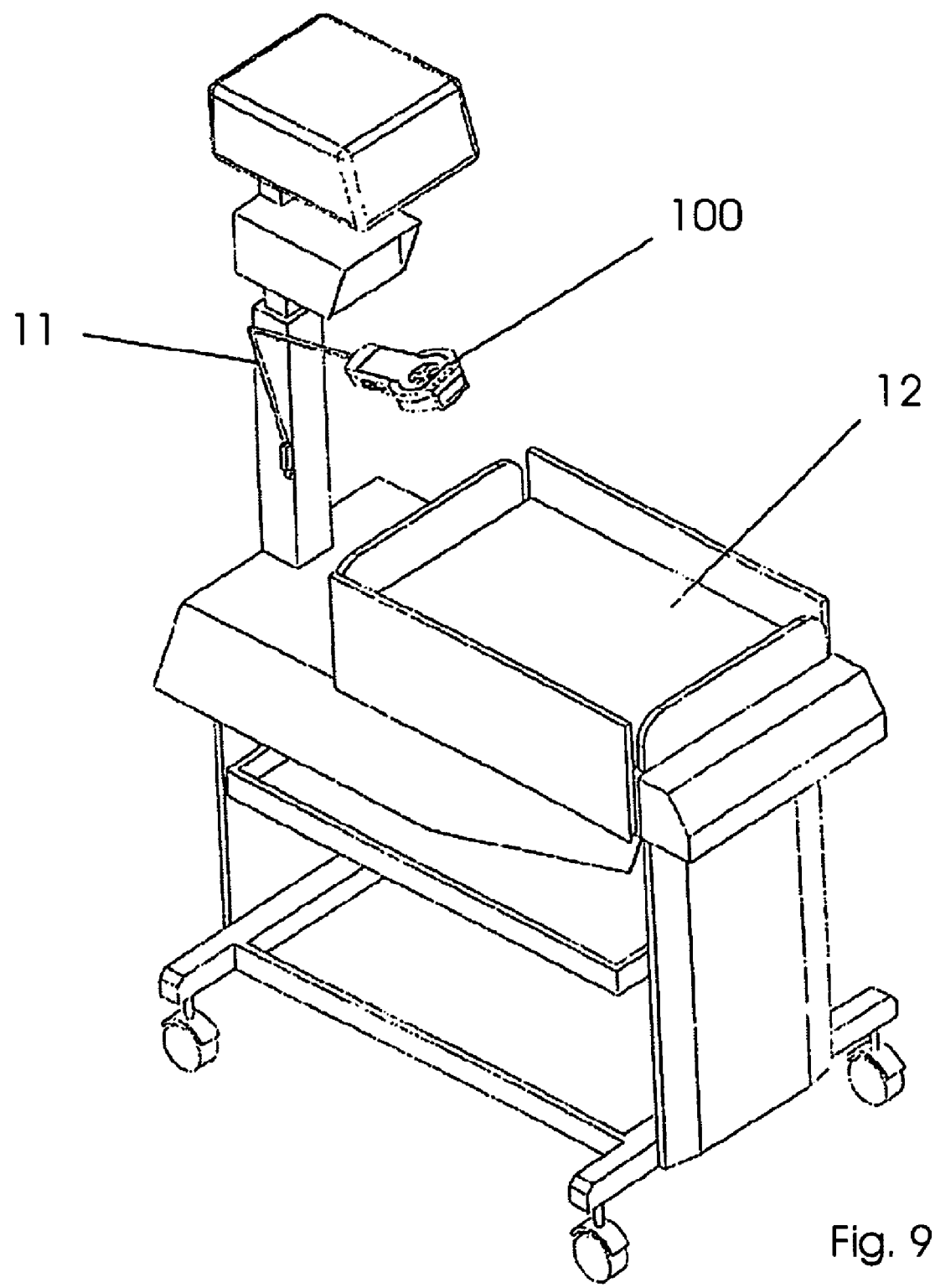
FIG. 9—is a perspective view of a generic cradle for newborns, equipped with the phototherapeutic equipment subject matter hereof, installed at the end of a system of articulable arm.
Figure 10:
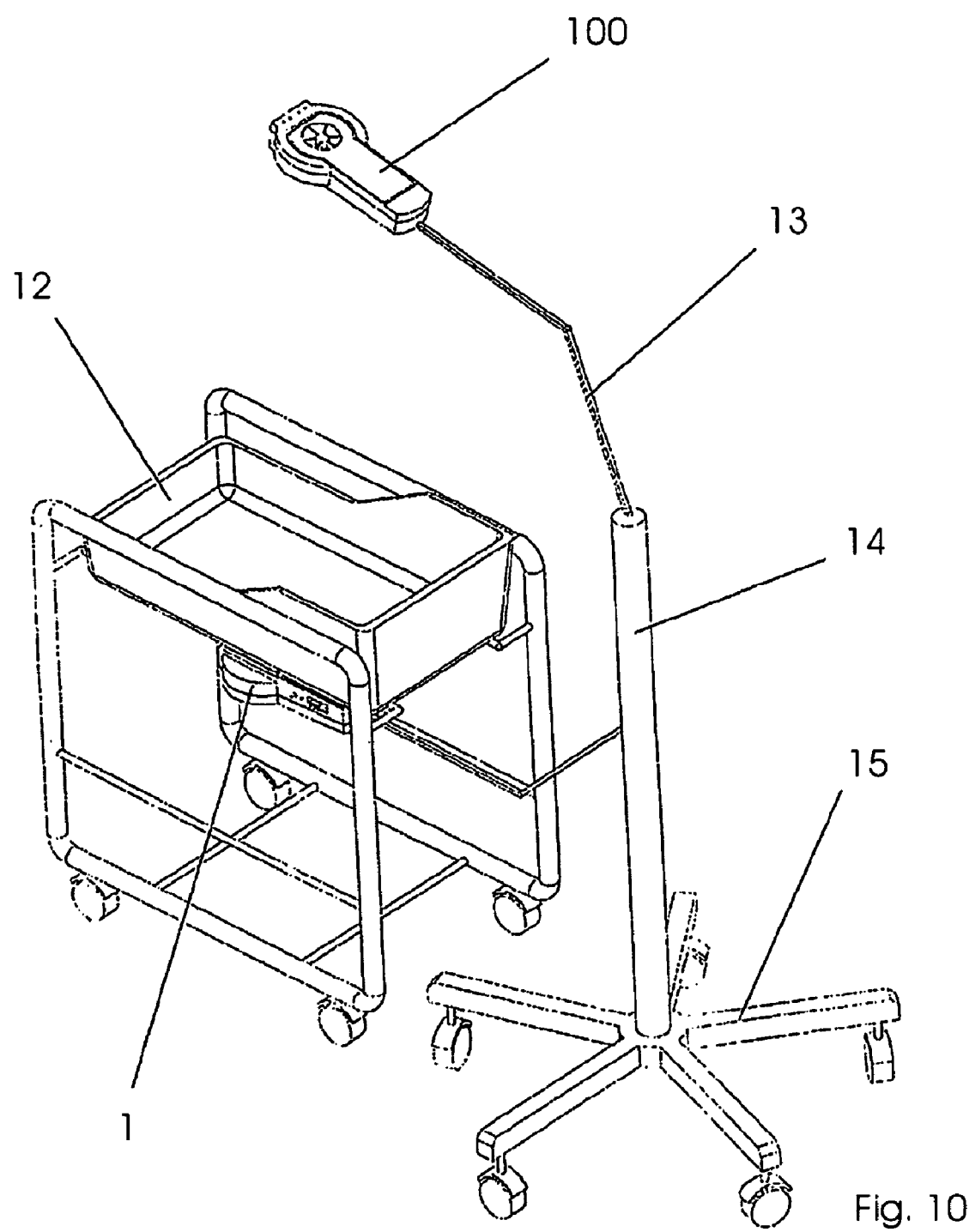
FIG. 10—is a perspective view of the phototherapeutic equipment of the present invention, positioned at the end of a movable rod, as showed in FIG. 8, positioned over a generic cradle.
Figure 17:
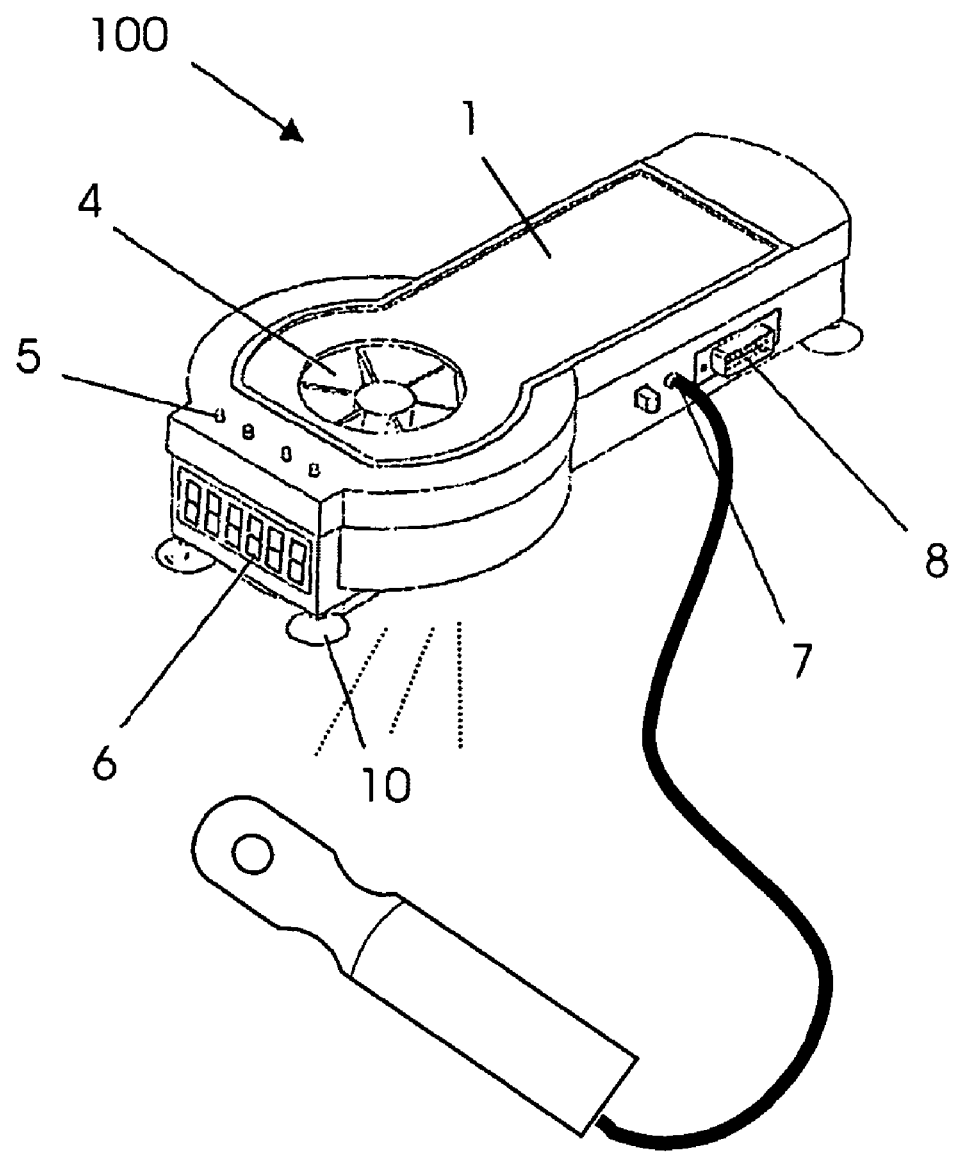
FIG. 17—is a schematic view of the equipment hereof associated with an optic probe.

As previously mentioned, the equipment 100 comprises at least one connector (7) for optical sensor (particularly illustrated in FIGS. 1, 3 and 4). Preferably, the optical sensor used is an optical probe (see FIG. 17), whose function is primarily the light intensity measurement. Based on value measured, it is possible to modify operation of the equipment 100 so as to provide the patient under treatment with optimum irradiance and intensity, on a case by case basis (which will be hereinafter described in details). It only is possible due to the existence of the microprocessor.

Obviously, other connectors can be provided for connection of other sensors, e.g., a sensor for measuring the distance between light emitting source and the patient (which allows to change irradiance value—see graph 2 above), a sensor for checking the level of bilirubin in patient's body or further any other as required or desired.

Another very important and advantageous characteristic of the phototherapy equipment 100 is that it is preferably microprocessed, i.e., it comprises at least one internal processing element (not illustrated), as a microprocessor (microchip).

The processor may present any configuration as required or desired, however whatever it may be, the equipment 100 should be able to perform a series of tasks which is possible only with the use of microprocessor.

Figure 18:
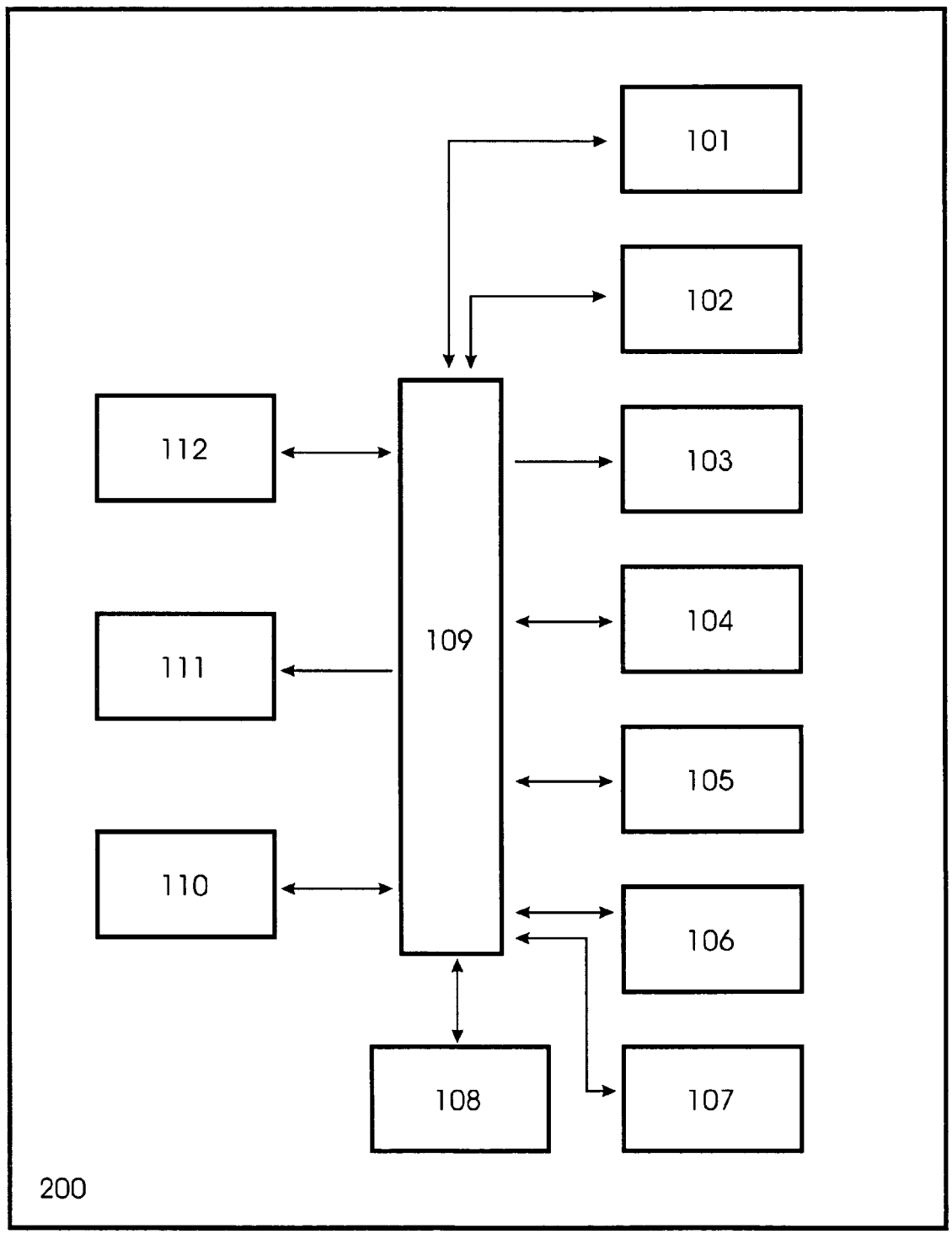
FIG. 18—is a schematic view of equipment management 200 of the equipment subject matter hereof.
Figure 19:
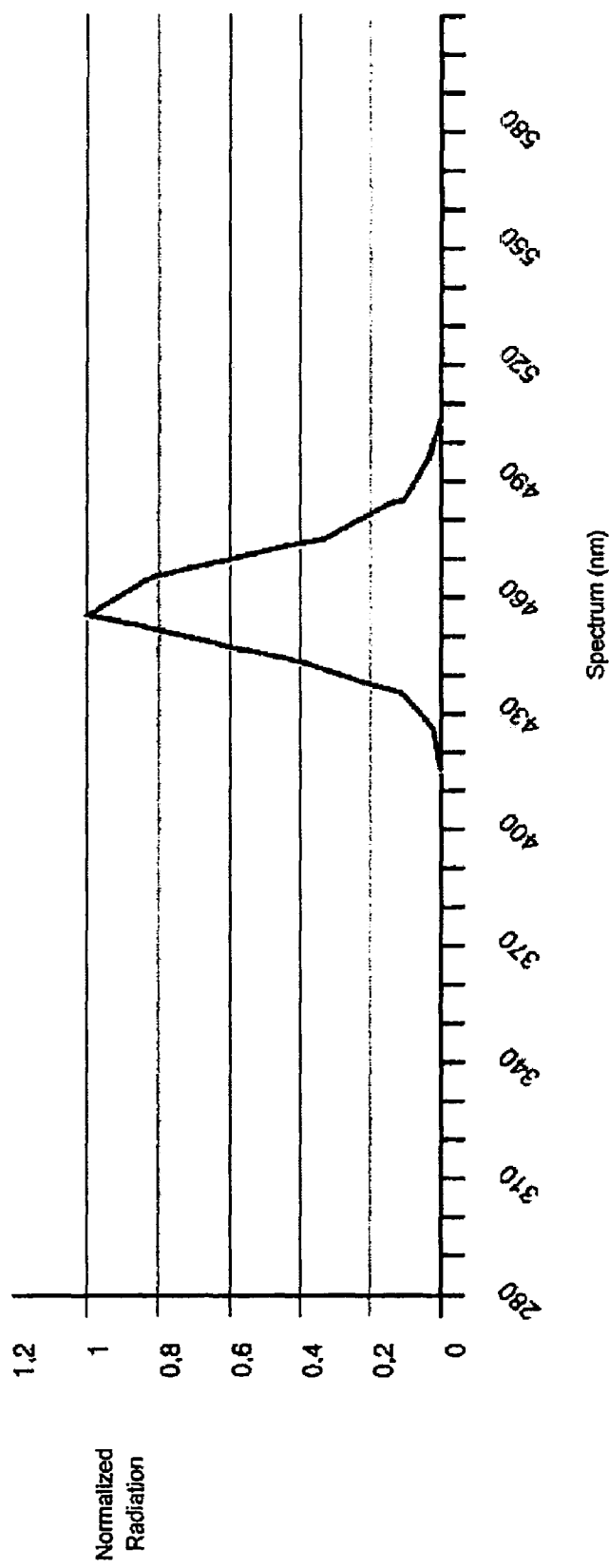
FIG. 19—is an illustration of normalized spectral irradiance of the equipment source across a spectrum of 280 nm to 600 nm.
Figure 20:
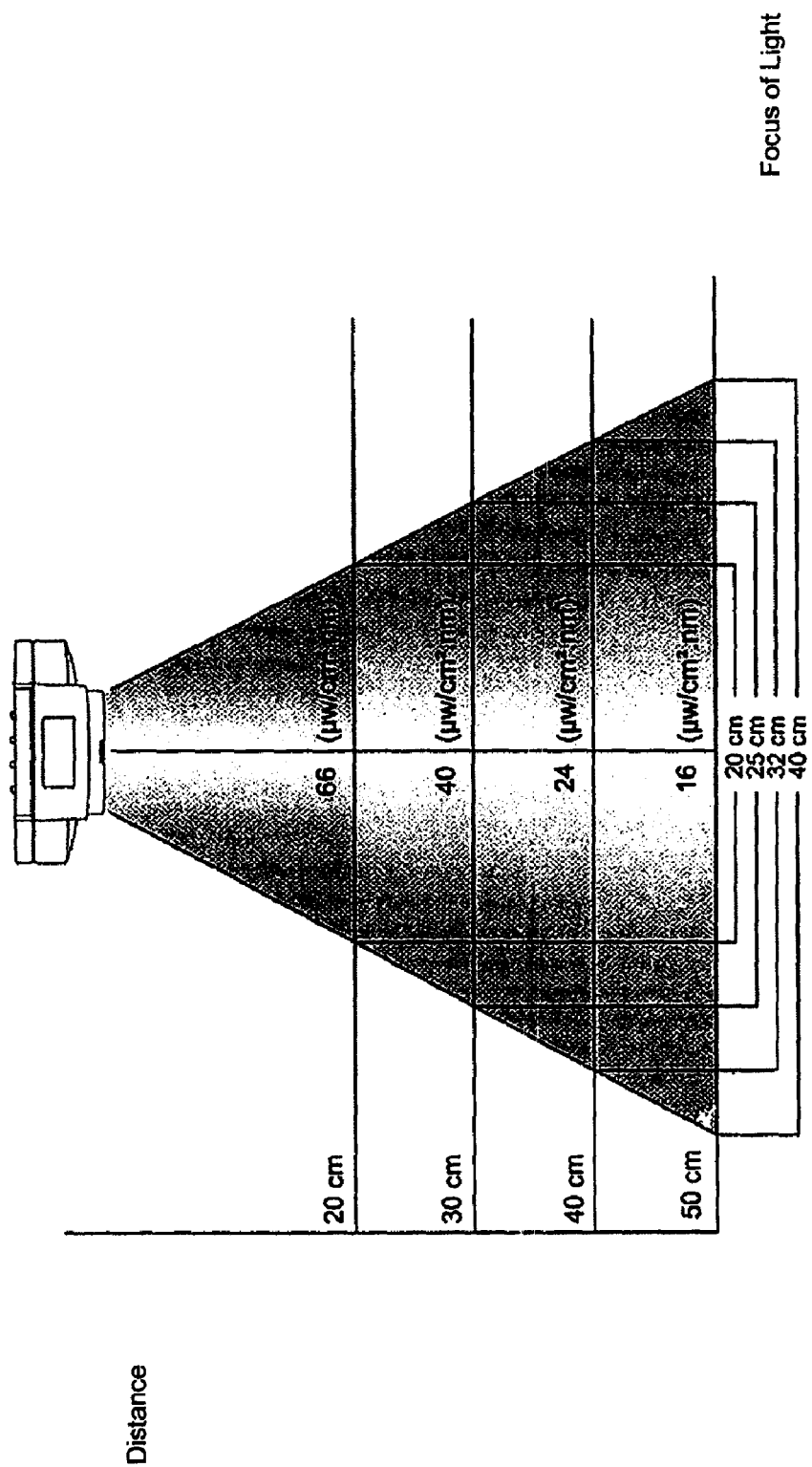
FIG. 20—is an illustration of a relationship between an application distance and a light focus of the equipment source.
Figure 21:
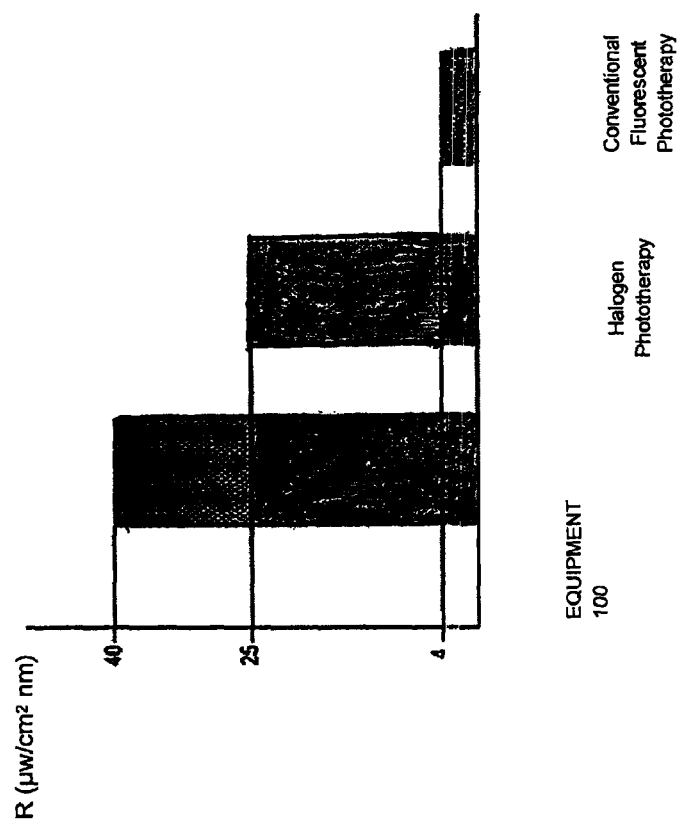
FIG. 21—is a comparative illustration of the light intensity capabilities of various phototherapy equipment that use halogen and fluorescent lamps.
Figure 21:
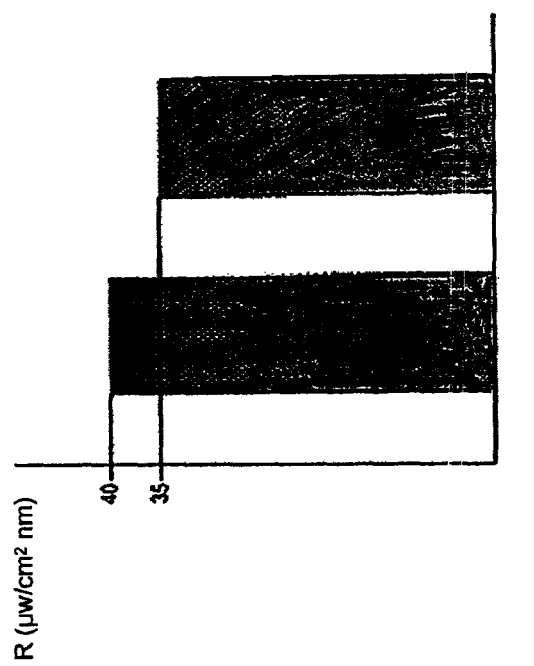

In order to enable operation of the equipment 100 provided with a microprocessor, a management system for the equipment 100 is provided, as illustrated in FIG. 18, composed by the following elements:

Clock 101;
Subroutine for selection of idiom used 102;
Subroutine for display of information 103;
Subroutine for detection of LED's operation time detection 104;
Subroutine for detection of phototherapy application time to a patient 105;
Subroutine for irradiance adjustment 106;
Subroutine for sensor data entry 107;
Subroutine for operation/programming data entry 108;
Subroutine for information analysis and processing 109;
Memory 110;
Subroutine for information transmission 111;
Subroutine for power source selection 112.

Whenever the equipment 100 under the present invention is placed to operate (either for the first time or not), operation of management system 200 is initiated, information being processed by microprocessor.

At least in the first time the equipment 100 is turned on, both clock 101 containing information regarding date (day, month and year), time (hours, minutes and seconds), and the programmable chronometer should be adjusted.

The clock is driven by handling the control and programming actuators 5 or further remotely, through connection 8 which may be coupled to a microcomputer or related equipment. In electronic terms, information for clock 101 adjustment is forwarded by subroutine for operation/programming data entry 108 and processed by subroutine for information analysis and processing 109. After this processing, the clock is driven. The clock 101 can be adjusted whenever required or desired, as indicated above.

Analogically, the idiom according to which the equipment operates can be adjusted, and further by handling control or programming actuators 5 or further remotely, through connection 8 which can be coupled to a microcomputer or related equipment. In electronic terms, information for idiom adjustment are forwarded by subroutine for operation/programming data entry 108 and processed by subroutine for information analysis and processing 109. After this processing, subroutine for selection of idiom used 102 activates a certain idiom (e.g.: Portuguese or English) and every information treated begins to be supplied in the idiom requested. The idiom can be adjusted whenever required or desired, as indicated above.

After adjusting the clock 101 and selecting the idiom, one should insert information regarding the patient to be treated in order to obtain operating characteristics of the equipment 100, aiming to maximize treatment effectiveness and patient's integrity.

Information regarding the patient (e.g.: name, age, degree of disease, weight, body area, sex, other information regarding registration etc.), should be also inserted by handling the control and programming actuators 5 or further remotely, by connection 8 which may be coupled to a microcomputer of related equipment. In electronic terms, information for idiom adjustment are forwarded by subroutine for operation/programming data entry 108 and processed by subroutine for information analysis and processing 109. After this processing, several parameters of the equipment 100 are adjusted in order to provide that optimized treatment.

In function of information regarding the patient, the subroutine for detection of phototherapy application time to a patient 105 and subroutine for irradiance adjustment 106 should be activated in order that the optimum treatment point may be reached. Obviously, activation of these subroutines can be manual, by the own operator (for example, by adjusting LED's 20 radiance level in function of the patient) or automatically, from the processing performed by the subroutine for information analysis and processing 109. As soon as the treatment begins, the subroutine for detection of phototherapy application time to a patient 105 enables the activation of the clock 101 aiming to determine patient's treatment time.

Modification of LED's 20 radiance is controlled by means of a analog digital converter (not illustrated), which converts the numerical value processed from the reading of the respective sensor into a direct current voltage value which may be modified to change LED's luminosity.

After beginning the treatment, several sensors may send information (e.g.: for assisting the treatment and measuring patient evolutions), from the subroutine for sensor data entry 107. Information supplied by these sensors are then processed by subroutine for information analysis and processing 109. Concurrently, information on treatment time provided by the clock are processed as well.

As previously mentioned, sensors may be the most varied ones, such as an optical sensor, like an optical probe, a sensor for measuring the distance between the light emitting source and the patient, a sensor for checking patient's body bilirubin level or further any other as required or desired.

In function of result processed by the subroutine for information analysis and processing 109 (that is, the meaning of information sent by sensors), the subroutine for display of information 103 displays results of sensors and processing (e.g.: by determining that the irradiance will be excessive, or that the patient should be placed near light source, or further any other situation).

Concurrently or not to display of that information, one may activate the subroutine for radiance 106 adjustment, either manually by the own operator (for example, by adjusting LED's 20 radiance level in function of the patient) or automatically, from the processing performed by subroutine for information and processing analysis 109.

Message issued may even determine the completion of the treatment, which may occur either manually or automatically, if the equipment 100 has that property.

During and after completion of the treatment, related information are stored in a memory 110, which will enable the equipment 100 to generate reports in respect of the treatment, whenever required. Memory 100 capability and the term during which information is stored may vary as required or desirable. That information may even be programmed by manipulation of control and programming actuators 5, or further remotely, by connection 8 which may be coupled to a microcomputer or related equipment. In electronic terms, at the time that adjustment occurs, information is sent by the subroutines to operation/programming data entry 108 and processed by subroutine for information 109 analysis and processing. After that processing, behavior and memory characteristics are modified.

At any time, before, during or after the treatment, reports containing varied information (such as time of treatment, irradiance emitted by LED's, patient's response level etc.) can be generated. These reports can be generated based on information contained in the memory 110 or otherwise concurrently with information processing by the information 109 analysis and processing subroutine.

Reports generated can be printed in a printer associated with equipment 100 in its serial output 8 or further in a remote printer associated with a computer. Alternately, should the equipment 100 be connected with an intranet or Internet network, by means of cabling or wireless connection, it is possible to send these reports to remotely-positioned computers (for example, those located in a central room of a lying-in hospital). The sending of information either to printer or to computers which are either remotely or physically connected with the equipment 100 is managed by the information transmission subroutine 111, which obviously makes transmission of information feasible through connection 8 (output gate) of equipment 100.

When the equipment 100 operates with electrical power, and a cut in its operation occurs during the treatment, the existing internal battery maintains it under operation and enables the storage of every information regarding patient's treatment. Battery lifetime may vary in a significant manner in function of its technical characteristics and also in function of the use of the equipment. Preferably, in order to provide operation of equipment 100 with direct current, a transforming source into alternating current is supplied (not illustrated).

When a cut in outside power supply occurs, the subroutine for selection of power supply 12 automatically directs the battery to feed the equipment 100, thereby providing the continuance of operation thereof.

Another important characteristic of the equipment 100 is to provide the information regarding LED's 20 lifetime, before the light properties it emits may suffer deterioration.

As previously mentioned, a LED 20 has a lifetime estimated in 20,000 to 50,000 hours, and, so far as this period is exceeded, light emitted by the same begins to loss the properties which make it so interesting for use in phototherapy, thus demanding replacement thereof. With the warning regarding the period of operations of LEDs, it is possible to accurately replace them at the end of their lifetime, without making use of inaccurate estimates. Moreover, the equipment 100 may operate as a phototherapy treatment valuator, as it enables to check whether it has been performed with LED's within or beyond their lifetime.

It should be mentioned that, in all operation situations as described above, the subroutine for information analysis and processing 109 is responsible for processing every information received by the equipment and further for that information stored in its memory 110, therefrom enabling to visualize information and thus modifying the equipment operation as well. It should be noted that without the existence of the processing element (not illustrated), none of those possibilities would be feasible.

Preferably, all above-described subroutines are part of an equipment management system 200 (computer program) specially developed for use in equipment 100, which may operate therein thanks to the processor. And, aiming to enable the correct operation of the equipment 100, the computer program is stored in the memory 110 and is placed into operation as soon the equipment 100 is turned on.

As advantages of the phototherapy equipment 100 provided with Nitride of Gallium and Indium LED's 20, the following can be mentioned, among many others:

possibility of increasing the distance between the light source and the patient, due to the high concentration of light in a relatively large area.

a significant reduction of the number of components and equipment size, thereby enabling a lower manufacturing, maintenance and operating cost, user friendly handling, as well as use and positioning in beds, incubators etc.

low consumption of electricity, due to the existence of few LED's 20 against hundreds LED of conventional equipment), which makes feasible the use of batteries (which is very important in case of lack of electric power, as usually happens in places with less resources).

high lifetime of LED's 20, compared with conventional halogen or fluorescent lamps (average lifetime of 20,000 to 50,000 hours, against 2,000 hours of halogen or fluorescent lamps).

light emission in blue spectrum, precisely in 450 nm wavelength, making the existence of filters for infrared and ultraviolet rays unnecessary (with the advantage of eliminating the possibility of burns, erythema and insensitive water loss). And, as conventional LED's are internally composed by Gallium Nitride (GaN), and LED's 20 are internally composed of Nitride of Gallium and Indium (InGaN), it will be never possible to obtain the same result in terms of efficacy of irradiance by using conventional LED's.

a significant reduction of heat issued, thereby enabling elimination of lenses to increase its efficiency, by installing mirror-shined cones which may be easily replaced for covering larger or smaller body surfaces, according to patient's anatomy, e.g., from premature children weighing 350 g to newborns of diabetic parents with more than 6 kg.

possibility of domiciliary use of the equipment 100, due to the non-emission of infrared and ultraviolet rays.

light focus on patient's body in a more defined and homogeneous manner, in the form of a circle of larger area, with reduced loss at the borders, thus enabling a more anatomic application to the patient's body;

attractive design, thereby reducing treatment oppression.

Thus, one can see from the foregoing that the phototherapy equipment 100 in question is characterized as a highly useful medical therapy appliance, preferably used in bilirubin treatment in newborns, presenting, as it has been shown, a plurality of differences regarding the conventional models existing in consuming market, in addition to technical constructive and functional characteristics which are completely different from those of the prior art.

After describing a preferred embodiment, it should be understood that the scope of the present invention covers other possible variations, it being limited only by the contents of the accompanying claims, which include the possible equivalents.

That which is claimed:

1. A phototherapy equipment, designed for the treatment of hyperbilirubinemia, comprising:
    at least one body provided with at least one phototherapic light source, in the form of at least one LED;
    an analog to digital converter;
    at least one sensor configured for sensing an intensity level of an irradiance emitted by the at least one LED;
    at least one internal processing element; and
    a management system enabled by the at least one internal processing element and configured to control the analog to digital converter to allow for a proportional adjustment of the irradiance emitted by the at least one LED, the proportional adjustment being based at least in part upon the irradiance sensed by the at least one sensor.

2. A phototherapy equipment according to claim 1, wherein the management system includes a computer program.

3. Equipment according to claim 2, wherein the computer program comprises the following subroutines:
- a subroutine for selection of idiom used;
- a subroutine for display of information;
- a subroutine for detection of LEDs operation time;
- a subroutine for detection of phototherapy application time to a patient;
- a subroutine for irradiance adjustment;
- a subroutine for sensor data entry;
- a subroutine for operation/programming data entry;
- a subroutine for information analysis and processing;
- a memory;
- a subroutine for information transmission; and
- a subroutine for power source selection, wherein the subroutines are processed by the at least one processing element.

4. A phototherapy equipment according to claim 3, wherein the body is substantially parallelepiped-shaped, comprising a first free end which is substantially cylindrical, wherein a diameter of the free end is substantially larger than the body width, creating two semicircular side projections.

5. A phototherapy equipment according to claim 4, wherein the body comprises at least one aperture configured to enable passage of air to be sucked and moved by a fan.

6. A phototherapy equipment according to claim 4, wherein the first free end, in a substantially cylindrical shape, comprises at least one control panel.

7. A phototherapy equipment according to claim 6, wherein the control panel is an alphanumerical liquid crystal display.

8. A phototherapy equipment according to claim 1, wherein the proportional adjustment of the irradiance emitted by the LEDs provides an optimum irradiance and intensity to treat the hyperbilirubinemia.

9. A phototherapy equipment, designed for the treatment of hyperbilirubinemia, comprising:
- at least one body provided with at least one phototherapic light source, in the form of at least one LED;
- at least one sensor configured for sensing an intensity level of an irradiance emitted by the at least one LED; and
- at least one internal processing element configured to:
  - process information regarding a lifetime of the at least one LED before light emission properties of the at least one LED suffer deterioration;
  - process information regarding the intensity level sensed by the at least one sensor; and
  - control an analog to digital converter to allow for a proportional adjustment of the irradiance emitted by the at least one LED, the proportional adjustment being based at least in part on the processed information regarding the lifetime and the intensity level.

10. A phototherapy equipment according to claim 9, wherein the proportional adjustment of the irradiance emitted by the LEDs provides an optimum irradiance and intensity to treat the hyperbilirubinemia.

11. A phototherapy equipment, designed for the treatment of hyperbilirubinemia, comprising:
- at least one body provided with at least one phototherapic light source, in the form of at least one LED;
- an analog to digital converter;
- at least one optical sensor;
- at least one sensor configured for sensing an intensity level of an irradiance emitted by the at least one LED; and
- at least one internal processing element configured to:
  - process information provided by the optical sensor;
  - process information provided by the least one sensor configured for sensing the intensity level; and
  - control the analog to digital converter to allow for a proportional adjustment of the irradiance emitted by the at least one LED, the proportional adjustment being based at least in part on the information provided by the optical sensor and the at least one sensor configured for sensing the intensity level.

12. A phototherapy equipment according to claim 11, wherein the proportional adjustment of the irradiance emitted by the LEDs provides an optimum irradiance and intensity to treat the hyperbilirubinemia.

13. A phototherapy equipment, designed for the treatment of hyperbilirubinemia, comprising:
- at least one body provided with at least one phototherapic light source, in the form of at least one LED;
- an analog to digital converter;
- at least one memory element;
- at least one sensor configured for sensing an intensity level of an irradiance emitted by the at least one LED;
- at least one sensor capable of sensing a distance between the at least one LED and a patient; and
- at least one internal processing element configured to:
  - process information on the distance provided by the at least one sensor;
  - control the analog to digital converter to allow for a proportional adjustment of the irradiance emitted by the at least one LED, the proportional adjustment being based at least in part on the information on the distance and the intensity level provided by the one or more of the at least one sensors.

14. A phototherapy equipment according to claim 13, wherein the proportional adjustment of the irradiance emitted by the LEDs provides an optimum irradiance and intensity to treat the hyperbilirubinemia.

15. A phototherapy equipment, designed for the treatment of hyperbilirubinemia, comprising:
- at least one body provided with at least one phototherapic light source, in the form of at least one LED;
- an analog to digital converter;
- an electromagnetic wave transmitting antenna for communication with a microcomputer;
- at least one sensor capable of sensing a patient's body bilirubin level;
- at least one sensor configured for sensing an intensity level of an irradiance emitted by the at least one LED; and
- at least one internal processing element configured to:
  - process information on the patient's body bilirubin level provided by the at least one bilirubin sensor;
  - process information provided by the least one sensor configured for sensing the intensity level; and
  - control the analog to digital converter to allow for a proportional adjustment of the irradiance emitted by the at least one LED, the proportional adjustment being based at least in part on the information on the patient's body bilirubin level and intensity level provided by the one or more of the at least one sensors.

16. A phototherapy equipment according to claim 15, wherein the proportional adjustment of the irradiance emitted by the LEDs provides an optimum irradiance and intensity to treat the hyperbilirubinemia.

17. A phototherapy equipment, designed for the treatment of hyperbilirubinemia, comprising:
- at least one body provided with at least one phototherapic light source, in the form of at least one LED;
- at least one optical sensor;
- at least one sensor configured for sensing an intensity level of an irradiance emitted by the at least one LED;

at least one sensor capable of sensing the distance between the LED and a patient;

at least one sensor capable of sensing the patient's body bilirubin level;

an analog to digital converter; and at least one internal processing element configured to enable irradiance adjustment by:

processing information provided by one or more of the at least one sensors; and controlling the analog to digital converter to allow for a proportional adjustment of the irradiance emitted by the LEDs, the proportional adjustment being based at least in part on the information provided by the one or more of the at least one sensors.

18. A phototherapy equipment according to claim 17, wherein the proportional adjustment of the irradiance emitted by the LEDs provides an optimum irradiance and intensity to treat the hyperbilirubinemia.

* * * * *